US012758690B2

(12) United States Patent
Liu et al.

(10) Patent No.: US 12,758,690 B2
(45) Date of Patent: Oct. 13, 2026

(54) WEARABLE BREAST PUMP

(71) Applicant: Guangdong Youmeng Electrical Technology Co., Ltd., Foshan City (CN)

(72) Inventors: Zongjun Liu, Foshan City (CN); Qiulin Zhang, Foshan City (CN)

(73) Assignee: Guangdong Youmeng Electrical Technology Co., Ltd., Foshan City (CN)

( * ) Notice: Subject to any disclaimer, the term of this patent is extended or adjusted under 35 U.S.C. 154(b) by 415 days.

(21) Appl. No.: 18/535,145

(22) Filed: Dec. 11, 2023

(65) Prior Publication Data

US 2024/0197971 A1 Jun. 20, 2024

(30) Foreign Application Priority Data

Dec. 19, 2022 (CN) ......................... 202211632483.8
Nov. 14, 2023 (CN) ......................... 202311514595.8

(51) Int. Cl.
*A61M 1/06* (2006.01)

(52) U.S. Cl.
CPC .............. *A61M 1/06* (2013.01); *A61M 1/062* (2014.02); *A61M 1/064* (2014.02); *A61M 1/067* (2021.05); *A61M 2205/123* (2013.01); *A61M 2210/1007* (2013.01)

(58) Field of Classification Search
CPC ........ A61M 1/06; A61M 1/062; A61M 1/064; A61M 1/067; A61M 2205/123; A61M 2210/1007
See application file for complete search history.

(56) References Cited

FOREIGN PATENT DOCUMENTS

CN 209451025 U * 10/2019
CN 115192800 A * 10/2022

OTHER PUBLICATIONS

English translation CN 115192800 A (2022).*
English translation CN 209451025 U (2019).*

* cited by examiner

*Primary Examiner* — John Kim
(74) *Attorney, Agent, or Firm* — Spencer Fane LLP

(57) ABSTRACT

The present disclosure relates to the technical field of mom and baby products, in particular, relates to wearable breast pump, comprising a breast pump principal machine and a breast pump container connected with each other detachably; the breast pump container includes a milk bottle and a breast suction shield connected with each other; the breast suction shield includes an absorption portion, a mating portion, and a suction portion that are integrated together; and the absorption portion is used to fit with a breast, the mating portion is used to connect to the breast pump principal machine, to form a sealing chamber between the breast pump principal machine and the suction portion, the suction portion is used to expand when the sealing chamber is under a negative pressure, suck milk.

9 Claims, 5 Drawing Sheets

WEARABLE BREAST PUMP

CROSS-REFERENCE TO RELATED APPLICATIONS

This application claims priority to Chinese Patent Applications Nos. 202211632483.8 filed in China on Dec. 19, 2022 and 202311514595.8 filed in China on Nov. 14, 2023. The entire disclosures of Chinese Patent Applications Nos. 202211632483.8 and 202311514595.8 are hereby incorporated herein by reference.

BACKGROUND

Field of the Invention

The present disclosure relates to the technical field of mom and baby products, in particular, relates to wearable breast pump.

Background Information

The wearable breast pump is placed under the bras for use. For example, a breast pump is referred to in a patent application document with application No. 201510647623.2 filed on Oct. 9, 2015 and invention title of "a breast pump adapted to be used when lying down and free of hands", which comprises components such as a bottom cover, an airbag, a casing, and a cup, wherein, as for the structural arrangement of the breast pump, the cup is sleeved on the outside of the casing, the casing is sleeved outside the airbag, thus the thickness of the breast pump is increased. Another breast pump is also referred to in a patent application document with application No. 202122735820.3 filed on Nov. 9, 2021 and invention title of "an integrated breast suction shield and an wearable breast pump therewith", which comprises components such as an integrated breast suction shield 100, a principal machine 2, a support bracket for a breast suction shield 4, a milk bottle main body 31, wherein, as for the structural arrangement of the breast pump, the principle machine is connected with the support bracket for the breast suction shield, the principle machine is connected with the milk bottle main body, and the support bracket for the breast suction shield is connected with the integrated breast suction shield. A support structure is provided between the integrated breast suction shield and the principle machine, thus the thickness of the breast pump is increased.

Therefore, at present, due to a product's large volume, the wearable breast pump on available is prone to cause uncomfortability by serious extrusion when in use. In addition, the wearable breast pump is also prone to cause unfitness due to a large volume, thus phenomenon of air leakage and milk leakage are occurred.

SUMMARY

In order to solve the above-mentioned problems, the present disclosure provides a wearable breast pump, and its technical solution is as follows:

The present disclosure provides a wearable breast pump, comprising a breast pump principal machine and a breast pump container connected with each other detachably; the breast pump container includes a milk bottle and a breast suction shield that are connected with each other; the breast suction shield includes an absorption portion, a mating portion, and a suction portion that are integrated together;

and the absorption portion is used to fit with a breast, the mating portion is used to connect to the breast pump principal machine, to form a sealing chamber between the breast pump principal machine and the suction portion, the suction portion is used to expand when the sealing chamber is under a negative pressure, to suck milk.

The wearable breast pump as above-mentioned, further preferably, a one-way sealing ring is provided on an end surface of the mating portion that faces the suction portion, the one-way sealing ring surrounds an outer side of the suction portion; the one-way sealing ring includes an abutting portion and a floated portion protruding from the end surface of the suction portion; the abutting portion is located between the floated portion and the suction portion, an end surface of the abutting portion that faces the breast pump principal machine is a plane, which is used to fit with the breast pump principal machine; and a cross section of the floated portion is an oblique triangle, and a top point of the triangle is inclined toward the breast pump principal machine, and an angle is formed between a side edge of the triangle adjacent to the mating portion and an end surface of the mating portion.

The wearable breast pump as above-mentioned, further preferably, the mating portion includes a mating base and a support ring that are integrated together, hardness of the support ring is larger than that of the mating base.

The wearable breast pump as above-mentioned, further preferably, a positioning groove is provided on a peripheral surface of the support ring, a spring positioning bead is provided on the breast pump principal machine, and the spring positioning bead and the positioning groove are connected in a clamped manner, to make the one-way sealing ring compress the breast pump principal machine.

The wearable breast pump as above-mentioned, further preferably, a bottom of the support ring is connected with a connecting pipe and a connecting cover, the support ring, the connecting pipe, and the connecting cover are integrated together; a bottom of the mating base is provided with a milk-leakage hole, and the connecting pipe is used to communicated with the milk-leakage hole and the connecting cover; the connecting cover includes an inner cover edge and an outer cover edge, the inner cover edge is connected with a one-way valve in a clamped manner, and the outer cover edge is connected with the milk bottle in a spinning manner; and an air hole is provided on the connecting cover.

The wearable breast pump as above-mentioned, further preferably, the support ring, the connecting pipe, and the connecting cover are connected with each other detachably, and the mating base and the support ring are connected with each other detachably.

The wearable breast pump as above-mentioned, further preferably, a circular groove is provided on the mating base, and a plurality of conjugation pores are provided on the circular groove, the plurality of conjugation pores are uniformly distributed on a peripheral surface of the circular groove; the support ring is in located the circular groove and a plurality of conjugation protrusions are provided on the support ring, the plurality of conjugation protrusions are uniformly distributed on the peripheral surface of the support ring; and the conjugation protrusions and the conjugation pores are plugged with each other one by one and integrated together.

The wearable breast pump as above-mentioned, further preferably, the support ring includes a pluggable ring and an epitaxial ring that are integrated together; the epitaxial ring is located between the pluggable ring and the absorption portion, and used to support the absorption portion; and the epitaxial ring is arranged coaxially with the absorption portion, and a profile of the epitaxial ring is small than that of the absorption portion.

The wearable breast pump as above-mentioned, further preferably, the pluggable ring is ellipse-shaped, and the major axis of the ellipse is arranged vertically, and the minor axis of the ellipse is arranged horizontally, and both ends along the direction of the minor axis each is provided with one positioning groove.

The wearable breast pump as above-mentioned, further preferably, the pluggable ring is circle-shaped, two positioning grooves are on both ends of the same diameter of the circle.

The wearable breast pump as above-mentioned, further preferably, a draft angle is provided on the peripheral surface of the pluggable ring.

The wearable breast pump as above-mentioned, further preferably, at the junction between the suction portion and the abutting portion, the suction portion is provided with an extended segment extending toward the absorption portion, and the extended segment is used to increase the deformation degree of the suction portion.

The wearable breast pump as above-mentioned, further preferably, the extended segment appears is arc-shaped, and the center of the arc is located between the extended segment and the suction portion.

The wearable breast pump as above-mentioned, further preferably, the suction portion is a chamber with a uniform wall thickness, the suction portion includes a suction body and guide ridges on the peripheral surface of the suction body that are integrated together, the guide ridges are used to guide deformation of the suction body.

The wearable breast pump as above-mentioned, further preferably, the guide ridges are provided with a plurality, and the plurality of guide ridges are distributed symmetrically on the peripheral surface of the suction body.

The wearable breast pump as above-mentioned, further preferably, the suction portion is cut-off along a plane parallel to the end surface of the mating portion, the profile of the guide ridges is U-shaped.

The wearable breast pump as above-mentioned, further preferably, the suction portion is cut-off along a plane perpendicularly to the end surface of the mating portion, the profile of the guide ridges is arc-shaped, and the center of the arc is closed to the suction body.

The wearable breast pump as above-mentioned, further preferably, the profile of the suction body is arc-shaped, and the center of the arc is closed to the guide ridges.

The wearable breast pump as above-mentioned, further preferably, comprising a floated emulating suction nozzle, the floated emulating suction nozzle is used for emulating a baby who is sucking the milk; the floated emulating suction nozzle is integrated with the breast suction shield.

The wearable breast pump as above-mentioned, further preferably, the floated emulating suction nozzle comprises a liquid suction hole, a floated support portion, and an emulating contact ring; the liquid suction hole is communicated with the floated support portion and the emulating contact ring, to allow a nipple to enter into the suction portion; the floated support portion is supported within the breast suction shield, the emulating contact ring is on an end surface of the floated support portion that is departed from the breast pump principal machine, to support a mammary areola; and the emulating contact ring is trumpet-shaped.

The wearable breast pump as above-mentioned, further preferably, the breast suction shield is provided with the emulating contact ring and the liquid suction hole, the emulating contact ring is on an end surface of the breast suction shield that is departed from the breast pump principal machine, to support the mammary areola; the liquid suction hole is communicated with the absorption portion and the suction portion; and the emulating contact ring is trumpet-shaped.

The wearable breast pump as above-mentioned, further preferably, the emulating contact ring is cut-off along a plane perpendicularly to the end surface of the mating portion, the profile of the emulating contact ring takes is arc-shaped, and the center of the arc is toward the breast suction shield.

The wearable breast pump as above-mentioned, further preferably, the emulating contact ring is cut-off along a plane perpendicularly to the end surface of the mating portion, the wall thickness of the emulating contact ring decreases gradually from the breast suction shield to a free end of the emulating contact ring.

The wearable breast pump as above-mentioned, further preferably, the breast pump principal machine comprises a casing and a control assembly, a T-pipe, an air pump, a solenoid valve, and a connecting port mounted within the casing; the control assembly is respectively connected with the air pump and the solenoid valve and used to offer an operation control; one end of the T-pipe is connected with the air pump, another end is connected with the solenoid valve, and the third one is communicated with the sealing chamber; and the connecting port is respectively connected with the air pump and the control assembly, and used to supply external power.

The wearable breast pump as above-mentioned, further preferably, the breast pump principal machine further comprises a battery mounted into the casing and connected with the connecting port, to supply power.

The wearable breast pump as above-mentioned, further preferably, the control assembly comprises a display screen, a control button, and a controller, the controller is respectively connected with the display screen, the control button, the air pump, the solenoid valve, and the connecting port, and the connecting port is a USB Type-C port.

As seen from analyses, compared with the prior art, the advantages and beneficial effects of the present disclosure are as follows:

- in the present disclosure, the wearable breast pump adopts a sealing chamber formed by the breast pump principal machine and the breast suction shield, can save the thickness space, and thus can avoid uncomfortability caused by extruding, furthermore, the present disclosure can improve fitness when in use, reduce air leakage and milk leakage. Furthermore, the wearable breast pump are mainly divided into two parts, one is a washable part of the breast pump container, another one is a non-washable part of the breast pump principal machine, and the breast pump container only includes two components of the milk bottle and the breast suction shield, thus parts are reduced and convenient to clean.

Wherein, 1—milk bottle, 2—breast pump principal machine, 3—control button, 4—display screen, 5—breast suction shield, 6—connecting port, 7—absorption portion, 8—emulating contact ring, 9—battery, 10—air pump, 11—T-pipe, 12—epitaxial ring, 13—positioning groove, 14—pluggable ring, 15—guide ridge, 16—suction body, 17—air hole, 18—one-way valve, 19—liquid suction hole, 20—floated support portion, 21—milk-leakage hole, 22—outer cover edge, 23—inner cover edge, 24—mating base, 25—floated portion, 26—abutting portion, 27—extended segment, 28—spring positioning bead, 29—sealing chamber.

DETAILED DESCRIPTION OF THE EMBODIMENTS

The following will provide a clear and complete description of the technical solution in the embodiments of the present disclosure, in conjunction with the attached drawings in the embodiments of the present disclosure. Obviously, the described embodiments are only a part of the embodiments of the present disclosure, not all of them. Based on the embodiments of the present disclosure, all other embodiments obtained by those skilled in the art without creative labor, fall within the scope of protection of the present disclosure.

In the description of this present disclosure, the orientation or positional relationships indicated by terms "longitudinal", "transverse", "up", "down", "front", "back", "left", "right", "vertical", "horizontal", "top", "bottom" etc. are based on the orientation or positional relationships shown in the attached drawings, only for the convenience of describing the present patent, rather than requiring that the present disclosure must be constructed and operated in a specific orientation, thus it cannot be understood as a limitation of the present patent. In the present disclosure, the terms as used "connected with each other" and "connected" should be broadly understood, for example, they can be fixed connection, they also can be detachable connection, they can be directional connection, and also they can be connected by an intermediate component. For those skilled in the art, the specific meanings of the above-mentioned terms can be understood based on specific circumstances.

Figure 1:
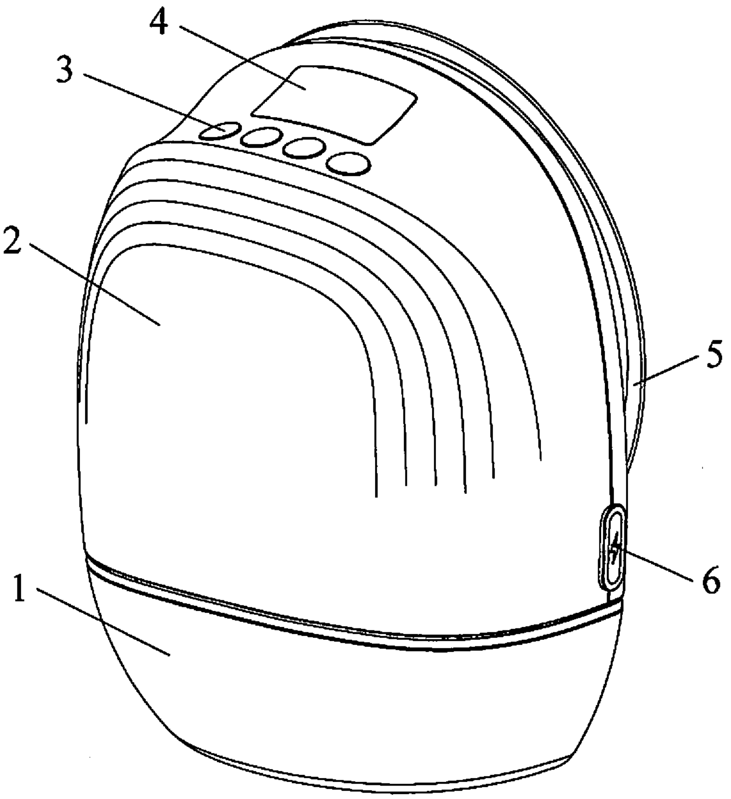
FIG. 1 is a structural schematic diagram 1 of a wearable breast pump of the present disclosure.
Figure 2:
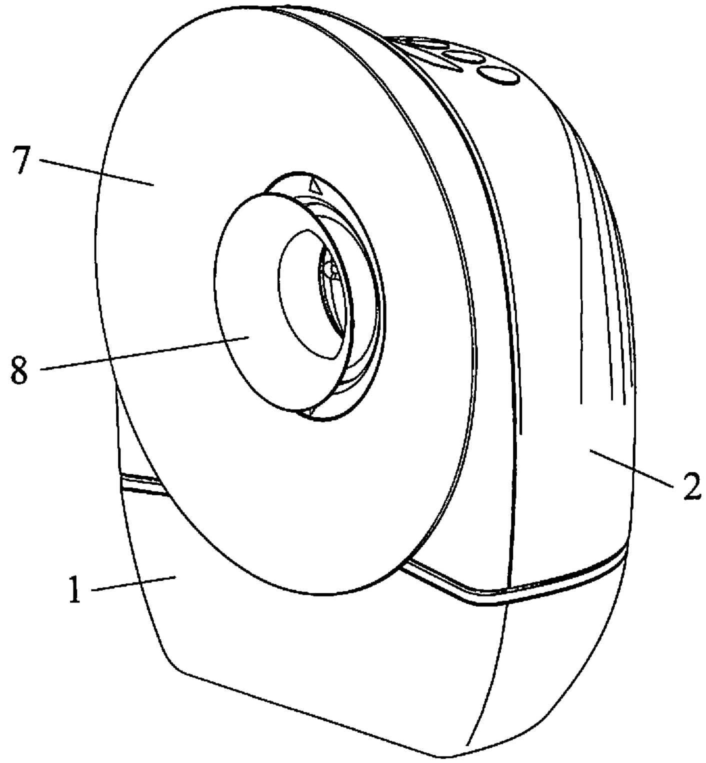
FIG. 2 is a structural schematic diagram 2 of a wearable breast pump of the present disclosure.
Figure 3:
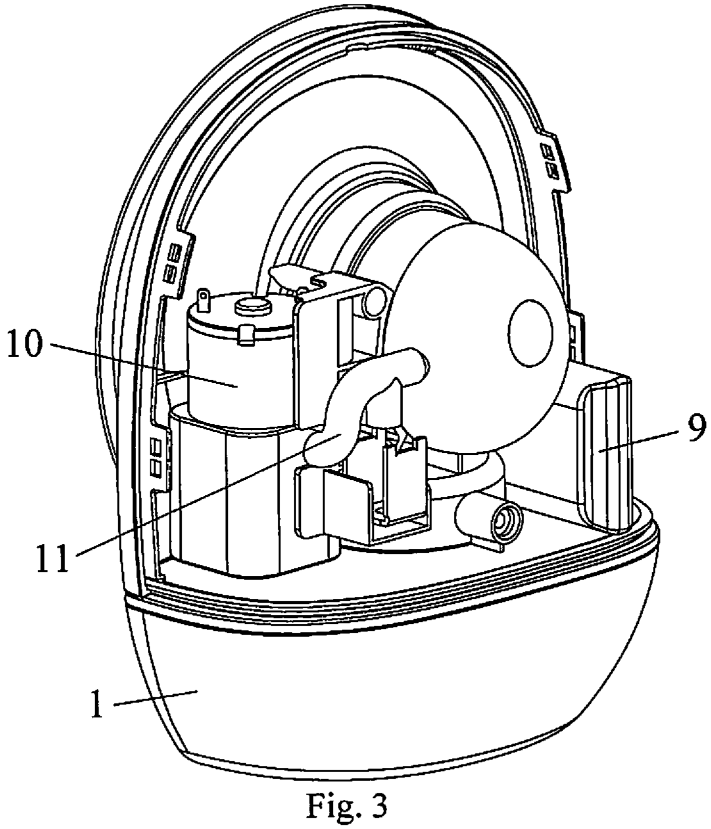
FIG. 3 is a schematic diagram of an internal structure of abreast pump principal machine of the present disclosure.
Figure 4:
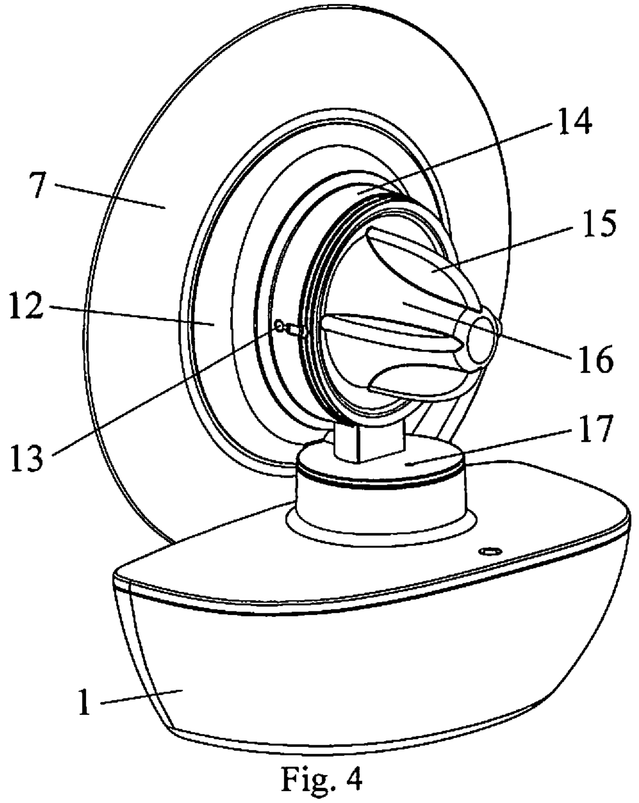
FIG. 4 is a structural schematic diagram of abreast pump container of the present disclosure.
Figure 5:
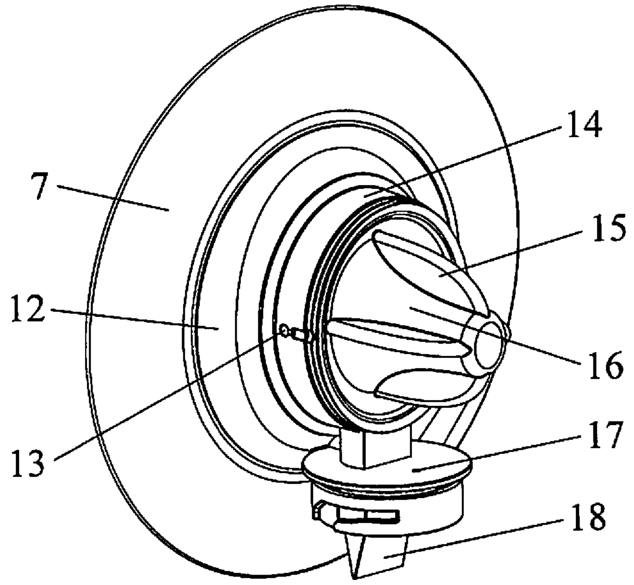
FIG. 5 is a structural schematic diagram of abreast suction shield of the present disclosure.
Figure 6:
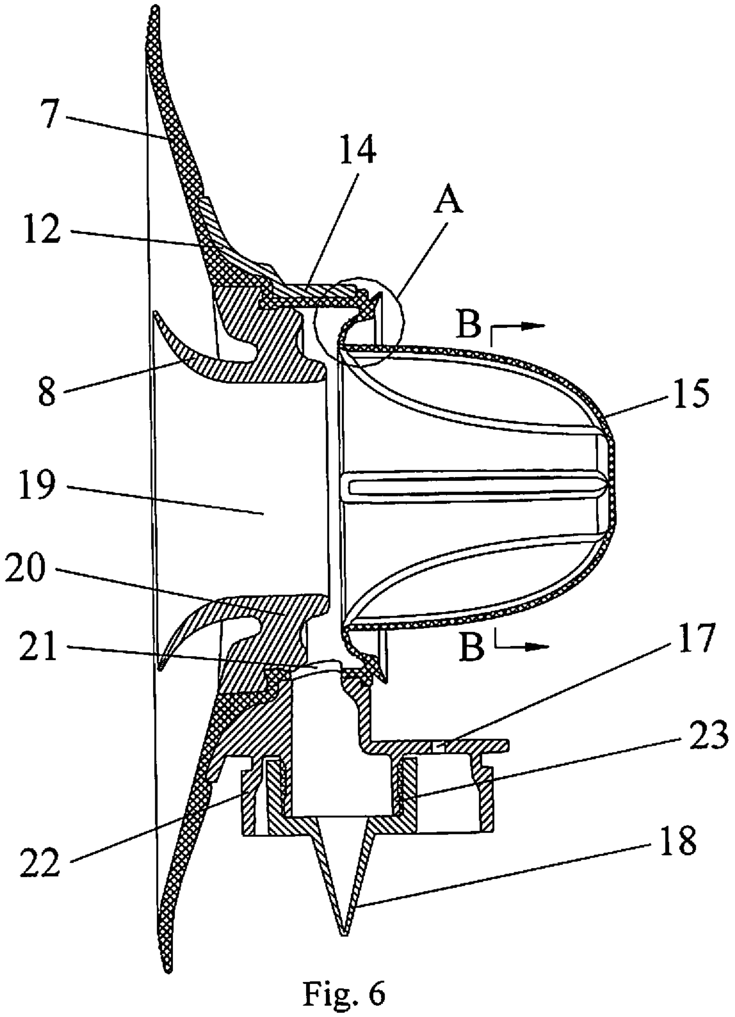
FIG. 6 is a sectional view of abreast suction shield of the present disclosure.
Figure 7:
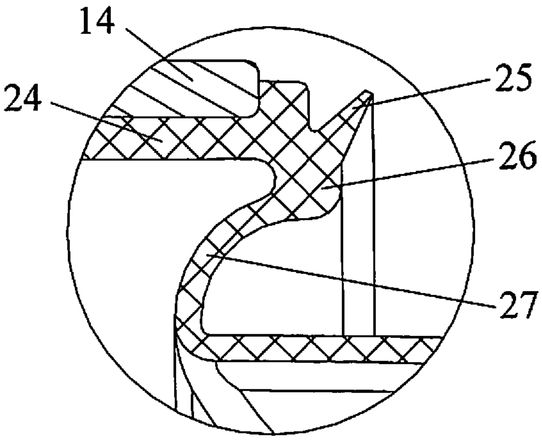
FIG. 7 is a partial enlarged view at A of FIG. 6 of the present disclosure.
Figure 8:
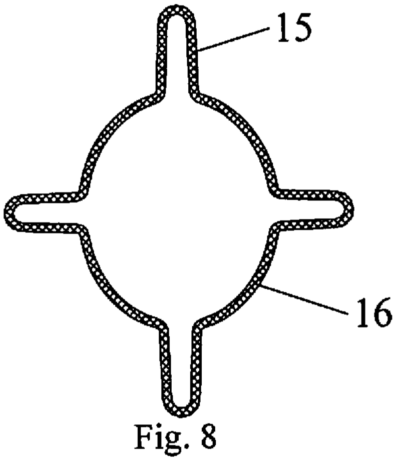
FIG. 8 is a cross-sectional view at B-B of FIG. 6 of the present disclosure.
Figure 9:
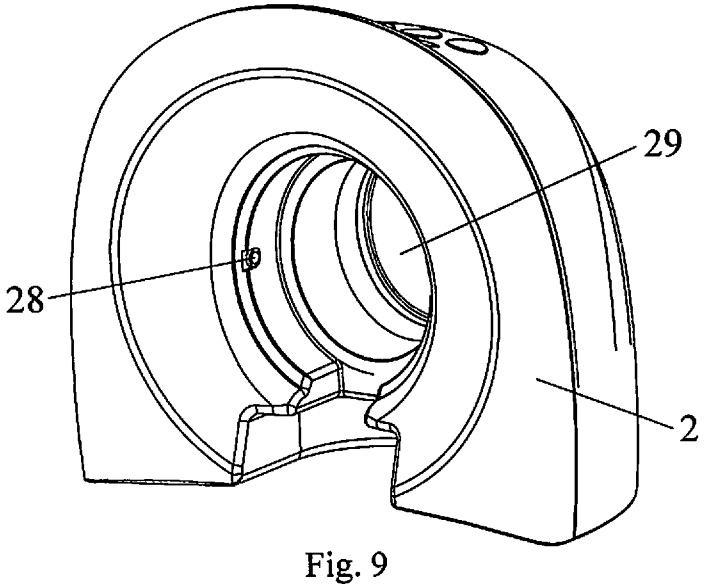
FIG. 9 is a structural schematic diagram of abreast pump principal machine of the present disclosure.
Figure 10:
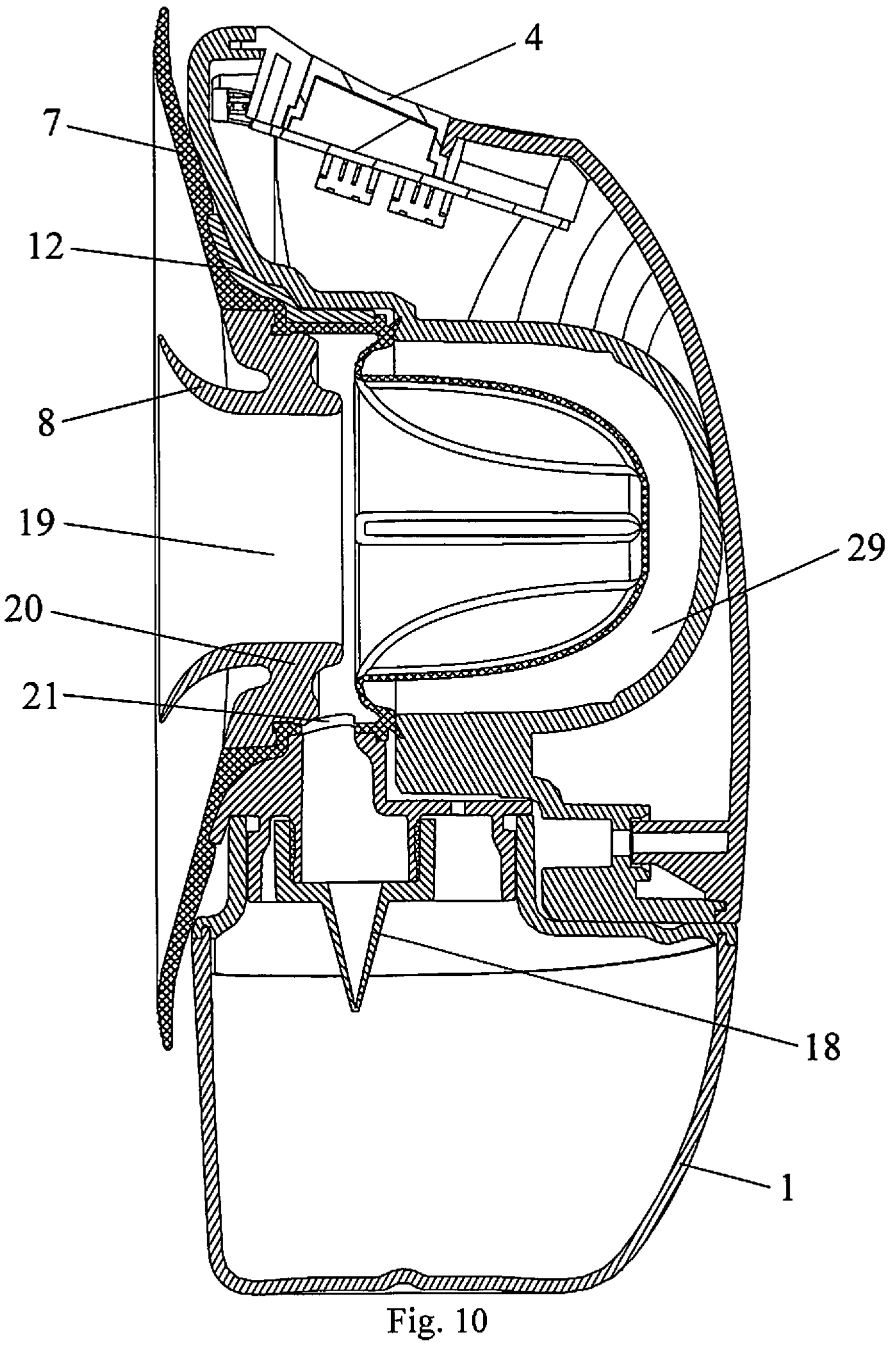
FIG. 10 is a sectional view of a wearable breast pump of the present disclosure.

Refer to FIGS. 1-10, wherein, FIG. 1 is a structural schematic diagram 1 of the wearable breast pump of the present disclosure; FIG. 2 is a structural schematic diagram 2 of a wearable breast pump of the present disclosure; FIG. 3 is a schematic diagram of an internal structure of abreast pump principal machine of the present disclosure; FIG. 4 is a structural schematic diagram of abreast pump container of the present disclosure; FIG. 5 is a structural schematic diagram of abreast suction shield of the present disclosure; FIG. 6 is a sectional view of abreast suction shield of the present disclosure; FIG. 7 is a partial enlarged view at A of FIG. 6 of the present disclosure; FIG. 8 is a cross-sectional view at B-B of FIG. 6 of the present disclosure; FIG. 9 is a structural schematic diagram of abreast pump principal machine of the present disclosure; FIG. 10 is a sectional view of a wearable breast pump of the present disclosure.

As shown in FIG. 1, FIG. 2, and FIG. 10, in one embodiment of the present disclosure, a wearable breast pump is provided. In particular, the wearable breast pump comprises a breast pump principal machine 2 and a breast pump container connected with each other detachably. Wherein, the breast pump container includes a milk bottle 1 and a breast suction shield 5 that are connected with each other. The breast suction shield includes an absorption portion 7, a mating portion, and a suction portion that are integrated together. When in use, the absorption portion 7 is used to fit with a breast; the mating portion is used to connect to the breast pump principal machine 2, to form a sealing chamber 29 between the breast pump principal machine 2 and the suction portion; the suction portion is used to expand when the sealing chamber 29 is under a negative pressure, to suck milk.

In the present embodiment, the wearable breast pump adopts the sealing chamber 29 formed by the breast pump principal machine 2 and the breast suction shield 5, can save the thickness space, and thus can avoid uncomfortability caused by extruding, furthermore, the present disclosure can improve fitness when in use, reduce air leakage and milk leakage. Furthermore, the wearable breast pump is mainly divided into two parts, one is a washable part of the breast pump container, and another one is a non-washable part of the breast pump principal machine 2. The breast pump container only includes two components of the milk bottle 1 and the breast suction shield 5, thus parts are reduced and convenient to clean.

As shown in FIG. 6, FIG. 7, FIG. 9, and FIG. 10, in one embodiment of the present disclosure, in order to ensure the tightness of the sealing chamber 29, a one-way sealing ring is arranged on an end surface of the mating portion that faces the suction portion, the one-way sealing ring surrounds the outer side of the suction portion, can be abutted against the breast pump principal machine 2, and seal the gap between the mating portion and the breast pump principal machine 2. In particular, the one-way sealing ring comprises an abutting portion 26 and a floated portion 25 protruding from an end surface of the suction portion. The abutting portion 26 is between the floated portion 25 and the suction portion, an end surface of the abutting portion 26 that faces the breast pump principal machine 2 is a plane, which can be fitted with the breast pump principal machine 2. The cross section of the floated portion 25 is an oblique triangle, and the top point of the triangle is inclined toward the breast pump principal machine 2, and an angle is formed between a side edge of the triangle adjacent to the mating portion and an end surface of the mating portion, when the abutting portion 26 is fitted with the breast pump principal machine 2, the floated portion 25 may deform with the action of extrusion force, thus the tightness of the sealing chamber 29 is ensured. Furthermore, in the present embodiment, the floated portion 25 is inclined toward the breast pump principal machine 2, and thus a one-way sealing effect is obtained when closing the sealing chamber 29, that is to say, the outside air cannot enter into the sealing chamber 29 through the floated portion 25, while gases within the sealing chamber 29 may be excluded to the outside through the floated portion 25, which is applied to negative pressure operating environment of the sealing chamber 29.

As shown in FIG. 6 and FIG. 7, in one embodiment of the present disclosure, the mating portion includes a mating base 24 and a support ring that are integrated together. Wherein, the hardness of the support ring is larger than that of the mating base 24, which can play a supporting role for the mating portion, and ensure the sealing effect between the mating portion and the breast pump principal machine 2.

Further, as shown in FIG. 4 and FIG. 9, in the present embodiment, a positioning groove 13 is arranged on the peripheral surface of the support ring, a spring positioning bead 28 is provided on the breast pump principal machine 2, and the spring positioning bead 28 and the positioning groove 13 are connected in a clamped manner, thus a detachable connection between the breast pump principal machine 2 and the breast pump container can be achieved. Moreover, when the spring positioning bead 28 and the positioning groove 13 are connected in a clamped manner, the end surface of the mating portion can be abutted against the breast pump principal machine 2, and then the one-way sealing ring compress the breast pump principal machine 2.

As shown in FIG. 6, in one embodiment of the present disclosure, the bottom of the support ring is connected with a connecting pipe and a connecting cover, the support ring, the connecting pipe, and the connecting cover are integrated together (i.e. the supporting ring, the connecting pipe, and the connecting cover are integrated into a whole unit after a process of vulcanization; or the supporting ring, the connecting pipe, and the connecting cover may be individually modeled through the process of vulcanization, then may be connected into an undetachable integrity by assembling, for example, the supporting ring, the connecting pipe, and the connecting cover may be connected together by ultrasonic welding after being individually modeled through the process of vulcanization), and thus the number of parts can be reduced and reliability of connection can be ensured. Wherein, the bottom of the mating base 24 is provided with a milk-leakage hole 21, and the connecting pipe can be communicated with the milk-leakage hole 21 and the connecting cover, the connecting cover can be connected with the milk bottle 1. When in use, the milk may be flowed to the connecting cover through the milk-leakage hole 21, and finally enter into the milk bottle 1. In the present embodiment, the supporting ring, the connecting pipe, and the connecting cover are integrated together, and then integrated with the breast suction shield 5, which can make the whole breast suction shield 5 into one unit, thus it is more convenient to clean.

It should be noted that, in the present disclosure, “integrated” means that one component immediately forms into an undetachable component when being manufactured using one material, for example, in the present embodiment, the pluggable ring 14 and the epitaxial ring 12 of the support ring are directly processed through vulcanization of an rubber material, one component is finished when being processed and is undetachable. “Integrated” means that two or more components being manufactured by different or identical materials, form into an undetachable component by hot melting, vulcanization, bonding etc., for example, in the present embodiment, the supporting ring, the connecting pipe, and the connecting cover may be individually molded, and then connected together by ultrasonic welding; in the present embodiment, the material of the support ring and that of other portions of the breast suction shield 5 are rubbers having different rigidities, the support ring and parts other than the support ring on the breast suction shield 5 are respectively modeled during the process of vulcanization, the support ring after being processed is one component, part other than the support ring on the breast suction shield 5 is another one component, these two components form into an undetachable breast suction shield 5 by hot melting, bonding etc. Of course, in other embodiments of the present disclosure, based on elements such as convenient processing, saving cost and easy maintenance and so on, the breast suction shield 5 may also be made detachable, for example, the supporting ring, the connecting pipe, and the connecting cover on the breast suction shield 5 all may be detached from the breast suction shield 5, and they are convenient to clean individually.

Further, in the present embodiment, the connecting cover includes an inner cover edge 23 and an outer cover edge 22, the inner cover edge 23 is connected with a one-way valve 18 in a clamped manner, and the outer cover edge 22 is connected with the milk bottle 1 in a spinning manner. The reliability of one-way flow of the milk can be ensured by providing the one-way valve 18; and a user is easy to pick off the milk bottle 1 and use by providing the spinning connection between the milk bottle 1 and the outer cover edge; and pressures in and out of the milk bottle 1 can be balanced by providing an air hole on the connecting cover.

In one embodiment of the present disclosure, in order to ensure the reliability of integration between the mating base 24 and the support ring, a circular groove is arranged on the mating base 24, and a plurality of conjugation pores are provided on the circular groove, the plurality of conjugation pores are uniformly distributed on the peripheral surface of the circular groove. The support ring is located in the circular groove, and a plurality of conjugation protrusions are provided on the support ring, the plurality of conjugation protrusions are uniformly distributed on the peripheral surface of the support ring; and the conjugation protrusions and the conjugation pores are plugged with each other one by one and can ensure that the mating base 24 and the support ring are integrated together.

As shown in FIG. 5 and FIG. 6, in one embodiment of the present disclosure, the support ring is made of rubber, the hardness of the support ring is larger than that of other rubber parts on the breast suction shield 5. The port ring includes a pluggable ring 14 and an epitaxial ring 12 that are integrated together. Wherein, the epitaxial ring 12 is between the pluggable ring 14 and the absorption portion 7, and can play a role of supporting the absorption portion 7, thus ensure the reliability of fitness of the absorption portion 7. In particular, the epitaxial ring 12 is arranged coaxially with the absorption portion 7, and the profile of the epitaxial ring 12 is small than that of the absorption portion 7, which can make the hardness of the central part of the absorption portion 7 is large and not easy to deform, while the hardness of the edge parts is small and easy to fit.

Further, in the present embodiment, the pluggable ring 14 may have various shapes, for example, the pluggable ring may take an ellipse or a circle shape etc. When the pluggable ring 14 is ellipse-shaped, and the major axis of the ellipse is arranged vertically, and the minor axis of the ellipse is arranged horizontally, it can ensure the correctness of connection between the breast suction shield 5 and the breast pump principal machine 2 and play an error-proof role. Both ends along the direction of the minor axis each is provided with one positioning groove 13, this can ensure the connecting reliability between the breast suction shield 5 and the breast pump container. When the pluggable ring 14 is circle-shaped, two positioning grooves 13 are on both ends of the same diameter of the circle, the pluggable ring 14 is more prone to be modeled, convenient to be manufactured, and easy to save cost when taking a circle shape.

Furthermore, in the present embodiment, a draft angle is provided on the peripheral surface of the pluggable ring 14, which is convenient for the breast suction shield 5 to be detached from the breast pump principal machine 2, and can ensure the sealing effect of connection.

As shown in FIG. 6, FIG. 7, and FIG. 10, in one embodiment of the present disclosure, the suction portion is connected with the abutting portion 26, moreover, at the junction between the suction portion and the abutting portion 26, the suction portion is provided with an extended segment 27 extending toward the absorption portion 7. When the sealing chamber 29 is under a negative pressure (less than the atmospheric pressure), the suction portion can be expand under the negative pressure, thus the pressure difference between the inside itself and the sealing chamber 29 is counteracted. When the suction portion expands, the arrangement of the extended segment 27 can make the absorption portion 7 expand toward the breast pump principal machine 2, thus the deformation degree of the suction portion can be increased and the effect of sucking the milk can be ensured.

Further, in the present embodiment, the extended segment 27 is arc-shaped, and the center of the arc lies between the extended segment 27 and the suction portion, which then can ensure the smoothness of the suction portion during expanding and contracting, and can ensure that the deformation of the suction portion is more gentle.

As shown in FIG. 5, FIG. 6, and FIG. 8, in one embodiment of the present disclosure, in order for the suction portion to be expanded and contracted, the suction portion is a chamber with uniform wall thickness, in particular, the suction portion includes a suction body 16 and guide ridges 15 on the peripheral surface of the suction body 16 that are integrated together, when in use, the guide ridges 15 are used to guide deformation of the suction body 16. Wherein, the suction portion is cut-off along a plane parallel to the end surface of the mating portion, and the profile of the guide ridge is U-shaped. When the air pressure in the sealing chamber 29 is negative, two side walls with U-shape of the guide ridges 15 can recover to natural shapes elastically under normal pressure, thus prompting the wall of the suction body 16 to be contracted.

Further, in the present embodiment, the suction portion is cut-off along a plane perpendicular to the end surface of the mating portion, and the profile of the guide ridge is arc-shaped, and the center of the arc is closed to the suction body 16, while the profile of the suction body 16 is arc-shaped, and the center of the arc is closed to the guide ridge 15, thus the expansion of the suction portion can be controlled, and the peripheral surface of the suction portion can expand gradually from the absorption portion 7 to the breast pump principal machine during expanding.

Furthermore, in the present embodiment, the guide ridges 15 are provided with a plurality, and the plurality of guide ridges 15 are distributed symmetrically on the peripheral surface of the suction body 16, which can make the suction portion uniformly expand and contract on the peripheral surface. Preferably, the guide ridges 15 have four, which can both prompt smooth and uniform expansion and contraction of the suction portion on the peripheral surface, and cannot hinder the expansion and contraction.

As shown in FIG. 2, in one embodiment of the present disclosure, the wearable breast pump further comprises a floated emulating suction nozzle, when in use, the floated emulating suction nozzle is used for emulating a baby sucking milk, which both can fit with the mammary areola and cooperate with the suction portion, and can squeeze a nipple open and closely, thus emulating a baby sucking the milk, it also can play a supporting role for the nipple, such that the sucked milk can flow into the milk bottle 1.

As shown in FIG. 6, in one embodiment of the present disclosure, the floated emulating suction nozzle is integrated with the breast suction shield 5. In particular, the floated emulating suction nozzle comprises a liquid suction hole 19, a floated support portion 20, and an emulating contact ring 8. The liquid suction hole 19 is communicated with the floated support portion 20 and the emulating contact ring 8, to allow the nipple to enter into the suction portion. The floated support portion 20 is supported within the breast suction shield 5 and connected with the breast suction shield 5 and the emulating contact ring 8. The emulating contact ring 8 is on the end surface of the floated support portion 20 that is departed from the breast pump principal machine 2, to support a mammary areola and make the nipple suspend within the suction portion. In addition, when in use, if the fitness between the absorption portion 7 of the breast suction shield 5 and the user is not tight and loose, the floated emulating suction nozzle may also compensate the air leakage caused by the unfitness.

In another one embodiment of the present disclosure, the floated emulating suction nozzle is not provided, rather, the emulating contact ring 8 and the liquid suction hole 19 are provided on the breast suction shield 5, that is to say, the emulating contact ring 8 directly acts as a part of the breast suction shield 5 when being integrated. In particular, the emulating contact ring 8 is located on the end surface of the breast suction shield 5 that is departed from the breast pump principal machine 2; and the liquid suction hole 19 is communicated with the absorption portion 7 and the suction portion.

As shown in FIG. 2 and FIG. 6, in one embodiment of the present disclosure, the emulating contact ring 8 is trumpet-shaped. In particular, the emulating contact ring 8 is cut-off along a plane perpendicular to the end surface of the mating portion, the profile of the emulating contact ring 8 is arc-shaped, and the center of the arc is toward the breast suction shield 5; the emulating contact ring 8 is cut-off along a plane perpendicular to the end surface of the mating portion, the wall thickness of the emulating contact ring 8 decreases gradually from the breast suction shield 5 to the free end of the emulating contact ring 8, thus ensuring the tightness and the fitness of the emulating contact ring 8 when in use and ensuring moderate hardness.

As shown in FIG. 3, in one embodiment of the present disclosure, the breast pump principal machine 2 comprises a casing and a control assembly, a T-pipe 11, an air pump 10, a solenoid valve, and a connecting port 6 mounted within the casing. In particular, the control assembly is respectively connected with the air pump 10 and the solenoid valve and can offer an operation control. One end of the T-pipe 11 is connected with the air pump 10, another end is connected with the solenoid valve, and the third one is communicated with the sealing chamber 29, when in use, the air pump 10 is started, and the solenoid valve can control the expansion and contraction of the suction portion by powering on and off. The connecting port 6 is respectively connected with the air pump 10 and the control assembly, and used to supply external power. Wherein, the control assembly comprises a display screen 4, a control button 3, and a controller. The controller is respectively connected with the display screen 4, the control button 3, the air pump 10, the solenoid valve, and the connecting port 6 and can off the operation control.

The control button 3 can regulate parameters of the controller, and the display screen 4 can display the regulated parameters.

Further, in the present embodiment, the breast pump principal machine 2 further includes a battery 9 mounted within the casing and connected with the connecting port 6, the battery 9 can supply power without external power and support the use of the wearable breast pump.

The connecting port 6 is a USB Type-C port and connected with the battery 9, can directly supply power and charge the battery when connecting with the external power.

As shown in FIG. 1 to FIG. 10, detailed description of working process of the present disclosure will be made below.

When in use, the power source is powered on, the battery 9 may be adopted to supply power or connected with the external power, and operational parameters of the breast pump principal machine 2 are regulated by the control button. The air pump 10 is started, the solenoid valve is powered on and off according to predetermined parameters as regulated. When the solenoid valve is off, the sealing chamber 29 has a negative pressure with the action of the air pump 10, the suction portion expands, and the emulating contact ring 8 extrudes the mammary areola and then sucks milk; when the solenoid valve is on, the inside of the sealing chamber 29 recovers to the atmosphere pressure, the suction portion contracts, and the emulating contact ring 8 expands. The solenoid valve is on and off uninterruptedly, which can emulate a scene that a baby is sucking the milk, and then the sucked milk enters into the milk bottle 1 from the milk leakage hole 21 through the connecting cover and the one-way valve 18. The one-way valve 18 acts to conduct in one-way manner, can allow the milk and gases to go through, rather than allowing the milk and gases to flow back, and can cooperate with the solenoid valve to form a sealing environment together.

As known by common technical knowledge, the present can be implemented through other schemes that are not departed from the spiritual essence or necessary features. Therefore, in terms of various prospects, the above-mentioned schemes are only exemplary descriptions, not limitation thereof. All changes fall within or equivalent to the scope of the present disclosure are included into the present disclosure.

What is claimed is:

1. A wearable breast pump, comprising:

a breast pump principal machine and a breast pump container connected with each other detachably, wherein the breast pump container includes a milk bottle and a breast suction shield connected with each other, the breast suction shield includes an absorption portion, a mating portion, and a suction portion that are integrated together, the absorption portion is used to fit with a breast, the mating portion is used to connect to the breast pump principal machine, to form a sealing chamber between the breast pump principal machine and the suction portion, the suction portion is used to expand when the sealing chamber is under a negative pressure, to suck milk, a one-way sealing ring is provided on an end surface of the mating portion that faces the suction portion, the one-way sealing ring surrounds an outer side of the suction portion, the one-way sealing ring includes an abutting portion and a floated portion protruding from the end surface of the suction portion, the abutting portion is located between the floated portion and the suction portion, an end surface of the abutting portion that faces the breast pump principal machine is a plane, which is used to fit with the breast pump principal machine, across section of the floated portion is an oblique triangle, and a top point of the triangle is inclined toward the breast pump principal machine, and an angle is formed between a side edge of the triangle adjacent to the mating portion and an end surface of the mating portion.

2. The wearable breast pump according to claim 1, wherein the mating portion includes a mating base and a support ring integrated together, hardness of the support ring is larger than that of the mating base, a positioning groove is provided on a peripheral surface of the support ring, a spring positioning bead is provided on the breast pump principal machine, and the spring positioning bead and the positioning groove are connected in a clamped manner, to make the one-way sealing ring compress the breast pump principal machine.

3. The wearable breast pump according to claim 2, wherein a bottom of the support ring is connected with a connecting pipe and a connecting cover, the support ring, the connecting pipe, and the connecting cover are integrated together, a bottom of the mating base is provided with a milk-leakage hole, and the connecting pipe is used to communicated with the milk-leakage hole and the connecting cover, the connecting cover includes an inner cover edge and an outer cover edge, the inner cover edge is connected with a one-way valve in a clamped manner, and the outer cover edge is connected with the milk bottle in a spinning manner, an air hole is provided on the connecting cover.

4. The wearable breast pump according to claim 2, wherein a circular groove is provided on the mating base, and a plurality of conjugation pores are provided on the circular groove, the plurality of conjugation pores are uniformly distributed on a peripheral surface of the circular groove, the support ring is located in the circular groove, and a plurality of conjugation protrusions are provided on the support ring, the plurality of conjugation protrusions are uniformly distributed on the peripheral surface of the support ring, the conjugation protrusions and the conjugation pores are plugged with each other one by one and integrated together.

5. The wearable breast pump according to claim 2, wherein the support ring includes a pluggable ring and an epitaxial ring integrated together, the epitaxial ring is located between the pluggable ring and the absorption portion, and used to support the absorption portion, the epitaxial ring is arranged coaxially with the absorption portion, and a profile of the epitaxial ring is small than that of the absorption portion.

6. The wearable breast pump according to claim 1, wherein at a junction between the suction portion and the abutting portion, the suction portion is provided with an extended segment extending toward the absorption portion, and the extended segment is used to increase deformation degree of the suction portion, the extended segment is arc-shaped, and a center of the arc is located between the extended segment and the suction portion.

7. The wearable breast pump according to claim 6, wherein the suction portion is a chamber with a uniform wall thickness, the suction portion includes a suction body and a guide ridge located on a peripheral surface of the suction body that are integrated together, the guide ridge are used to guide deformation of the suction body, the guide ridge is provided with a plurality, and the plurality of guide ridges are distributed symmetrically on the peripheral surface of the suction body.

8. The wearable breast pump according to claim 1, wherein the wearable breast pump further comprises a floated emulating suction nozzle used for emulating a baby sucking milk, the floated emulating suction nozzle is integrated with the breast suction shield, the floated emulating suction nozzle comprises a liquid suction hole, a floated support portion, and an emulating contact ring, the liquid suction hole is communicated with the floated support portion and the emulating contact ring, to allow a nipple to enter into the suction portion, the floated support portion is supported within the breast suction shield, the emulating contact ring is located on an end surface of the floated support portion that is departed from the breast pump principal machine, to support a mammary areola, the emulating contact ring is trumpet-shaped.

9. The wearable breast pump according to claim 1, wherein the breast suction shield is provided with an emulating contact ring and a liquid suction hole, the emulating contact ring is located on an end surface of the breast suction shield that is departed from the breast pump principal machine, to support mammary areola, the liquid suction hole is communicated with the absorption portion and the suction portion, the emulating contact ring is trumpet-shaped.

* * * * *